(12) United States Patent
Giberson et al.

(10) Patent No.: US 6,329,645 B2
(45) Date of Patent: Dec. 11, 2001

(54) APPARATUS FOR DAMPENING STANDING WAVE PATTERN GENERATION IN MICROWAVE OVEN

(75) Inventors: Richard Thorp Giberson, Chico; Paul Alex Hansen, Anderson; S. K. Thurmond, Shasta Lake; Ted Pella, Redding, all of CA (US)

(73) Assignee: Ted Pella, Inc., Redding, CA (US)

( * ) Notice: Subject to any disclaimer, the term of this patent is extended or adjusted under 35 U.S.C. 154(b) by 0 days.

(21) Appl. No.: 09/798,676

(22) Filed: Mar. 2, 2001

Related U.S. Application Data

(60) Provisional application No. 60/187,219, filed on Mar. 3, 2000.

(51) Int. Cl.[7] .................................................. H05B 6/74
(52) U.S. Cl. ...................... 219/745; 219/732; 219/759; 219/762; 219/694; 333/228
(58) Field of Search ......................... 219/745, 759, 219/762, 694, 731, 730, 746, 763, 687, 688, 678; 333/227, 228

(56) References Cited

U.S. PATENT DOCUMENTS

| Re. 34,373 | 9/1993 | Collins et al. ............... 219/10.55 B |
|---|---|---|
| 3,582,598 | 6/1971 | Wincott ............................ 219/10.69 |
| 3,663,783 * | 5/1972 | McKague, Jr. et al. ............ 219/694 |
| 4,316,070 * | 2/1982 | Prosise et al. ....................... 219/745 |
| 4,341,227 | 7/1982 | Turner ................................. 128/804 |
| 4,462,412 | 7/1984 | Turner ................................. 128/804 |
| 4,640,280 * | 2/1987 | Sterzer ................................ 219/745 |
| 4,702,262 | 10/1987 | Anderson et al. .................. 128/804 |
| 4,795,649 * | 1/1989 | Kearns et al. ....................... 219/731 |
| 4,835,354 | 5/1989 | Collins et al. ............... 219/10.55 B |
| 4,874,915 * | 10/1989 | Harms et al. ........................ 219/745 |
| 4,980,529 | 12/1990 | Bolton ........................ 219/10.55 M |
| 5,064,981 | 11/1991 | Bolton .......................... 219/10.55 E |
| 5,683,381 | 11/1997 | Carr et al. ............................. 606/27 |
| 5,829,519 | 11/1998 | Uthe ...................................... 166/60 |
| 6,018,157 * | 1/2000 | Craft ................................... 219/762 |

OTHER PUBLICATIONS

Kok et al., "The Problem of Hot Spots . . . ", *Scanning* vol. 15, pp. 100–109, (1993).
Giberson et al., "Microwave Fixation: Understanding . . . ", *Microscopy Research and Technique*, 32:246–254 (1995).
Giberson et al., "Microwave Processing Techniques . . . ", *Methods in Molecular Biology*, vol. 117, pp. 145–158 (1999).

* cited by examiner

Primary Examiner—Philip H. Leung
(74) Attorney, Agent, or Firm—Flanagan & Flanagan; John R. Flanagan

(57) ABSTRACT

An apparatus for dampening standing wave pattern generation in a closed cavity of a microwave oven, includes a fluid table having an enclosure made of a microwave energy transparent material, such as plastic, and a structure, such as top flat platform held in place by the enclosure, for defining a processing surface for placement thereupon of samples to be processed, and a quantity of dielectric fluid contained by the enclosure so as to provide a large flat surface of the dielectric fluid beneath the flat platform and thus below the processing surface. The apparatus also includes mechanisms for recirculating the dielectric fluid to and from the enclosure and for cooling the dielectric fluid to maintain the dielectric fluid within a given narrow range of temperatures.

17 Claims, 2 Drawing Sheets

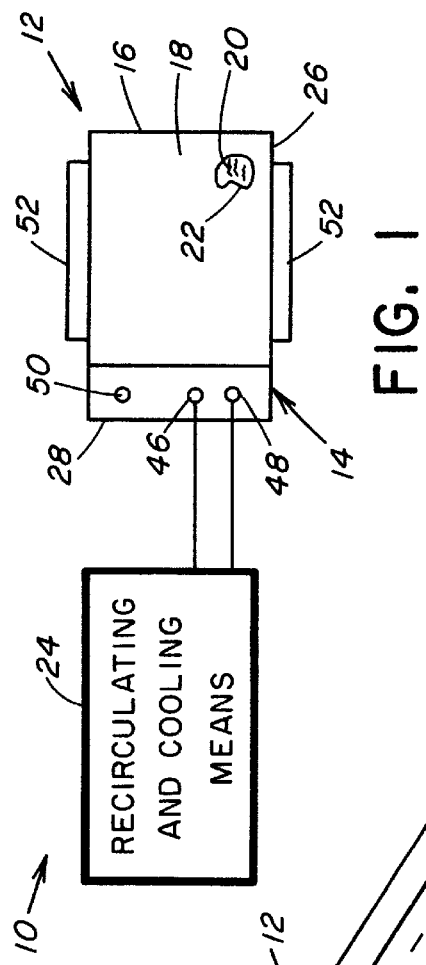
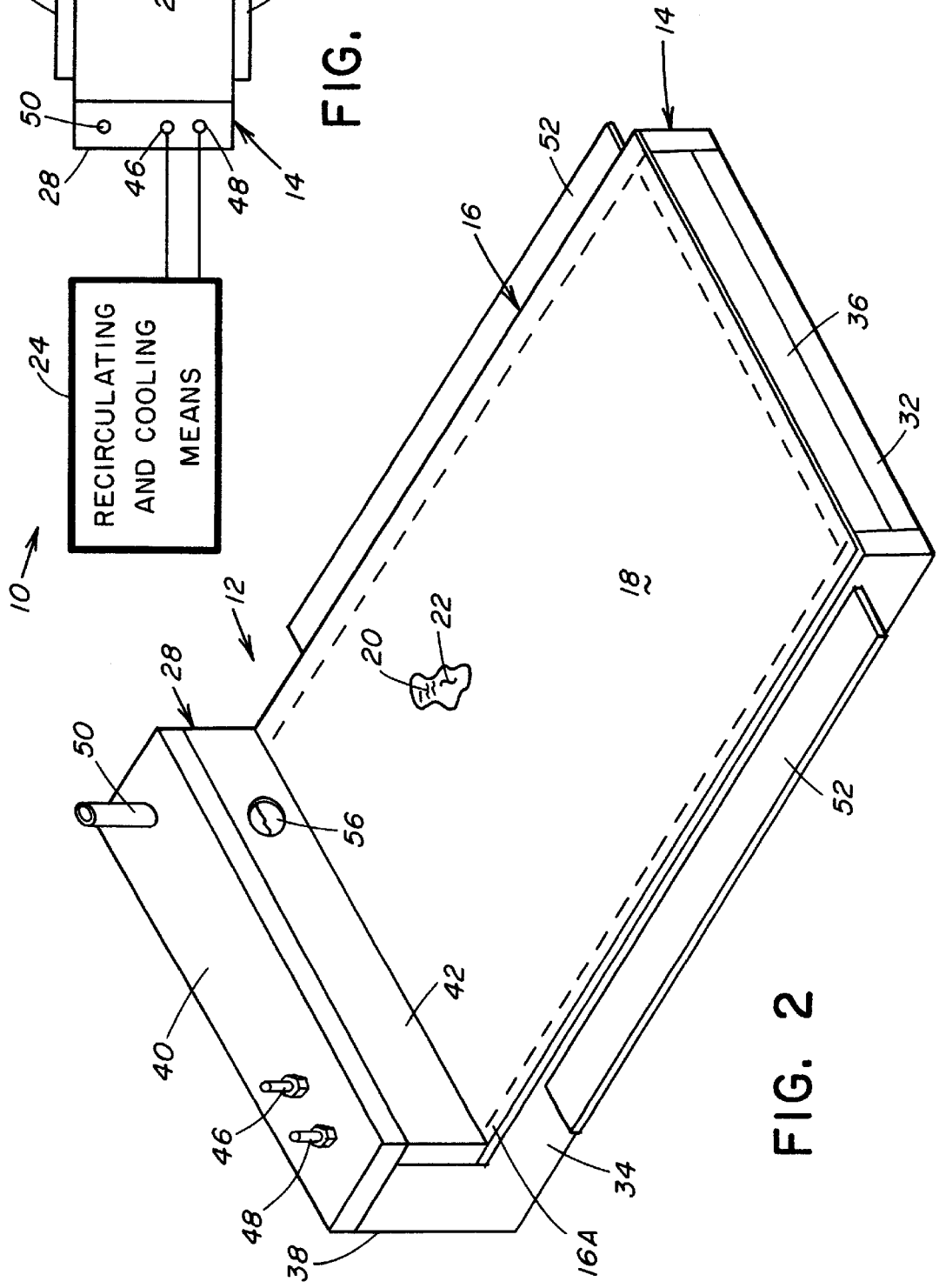

APPARATUS FOR DAMPENING STANDING WAVE PATTERN GENERATION IN MICROWAVE OVEN

This utility patent application claims the benefit of provisional application No. 60/187,219 filed Mar. 3, 2000.

BACKGROUND OF THE INVENTION

1. Field of the Invention

The present invention generally relates to sample processing in a microwave oven and, more particularly, is concerned with an apparatus for dampening standing wave pattern generation in a closed cavity of a microwave oven.

2. Description of the Prior Art

Automated mechanical and bench (hands-on) methods of sample processing are the standard practice today in research and clinical laboratories. Though relatively time-consuming, these methods are reliable in the sense that they provide reproducible results.

Over the last two decades there has been a growing interest in accelerating the steps required in processing of samples, such as tissue and other specimens, for research and clinical applications. Interest has focused on the use of microwave ovens which emit radiation at 2.45 GHz +/−50 MHz. The presence of microwave energy and its heating effects, produced via ionic conduction and dipole rotation, provide increased rates of heat diffusion which reduce overall processing times compared to mechanical or bench methods.

Uneven microwave induced specimen heating, however, is a problem. The closed cavity design of microwave ovens produces standing wave patterns which are characterized by regions of high to low electric field density. These regions cause uneven heating of samples during microwave exposure and are referred to as hot and cold spots. The non-uniform heating of samples placed at different locations in the microwave cavity affects run-to-run reproducibility.

To overcome problems with use of microwave ovens, users must be particularly mindful to keep processing conditions (e.g. sample container, fluid volume, container placement in microwave cavity, sample number, same microwave oven) the same for each run. Users typically take steps to identify hot and cold spots prior to actual sample processing by use of the conventional methods of recognition, such as thermographic paints, neon bulb arrays and liquid crystal sheets, in order to be able to select the correct container placement location. Also, users have recirculated a dielectric fluid, such as water, around a confined sample to help control rapid heating during microwave irradiation.

Dummy loads, usually a beaker filled with water primarily serving as a heat sink, are frequently used in the microwave cavity during sample processing. Also, it is known that the use of multiple water loads will produce relatively large areas of uniform energy for multiple sample processing. Kok et al. (Ref. 1) have disclosed that a flat layer of cold water in the microwave cavity is effective in reducing hot and cold spots. The dielectric properties of water, an absorptive material, are important when water is used as a static dummy load. It is known that as water heats its dissipation factor decreases and the penetration depth of microwave energy into the water increases. Giberson et al. (Refs. 2 & 3) have disclosed that the benefits of recirculation and cooling of water within the microwave cavity via the dummy or water load have been demonstrated during specimen processing. Also, Giberson et al. have disclosed that when the temperature of water can be held constant the microwave environment remains constant and relatively large areas of uniform heating can be created.

Although the potential benefits of water recirculation and cooling in microwave processing of samples are thus recognized and appreciated, there still exists an unfulfilled need for a device that will bring about the realization of these benefits in practice.

BACKGROUND REFERENCES

Ref. 1: Kok, L. P., Boon, M. E., Smid, H. M. 1993. The problem of hot spots in microwave equipment used for preparatory techniques—Theory and practice. *Scanning*, 15:100–109.

Ref. 2: Giberson, R. T., Demaree, R. S. Jr. 1995. Microwave fixation: Understanding the variables to achieve rapid reproducible results. *Micros. Res. Tech.* 32:246–254.

Ref. 3: Giberson, R. T., Demaree, R. S. Jr. 1999 Microwave processing techniques for electron microscopy: A four-hour protocol, In: *Methods in Molecular Biology.* N. Hajibagheri ed. Humana Press, Inc., Totowa, N.J., pp. 145–158.

SUMMARY OF THE INVENTION

The present invention provides an apparatus that satisfies the aforementioned unfulfilled need. As mentioned earlier, the closed cavity design of microwave ovens generates areas called hot and cold spots within the microwave cavity during periods of microwave irradiation at about 2.45 GHz. These areas have different energy densities and create regions having unequal heating properties. The apparatus of the present invention mitigates these areas of different energy densities and substantially minimizes these regions of unequal heating properties.

The apparatus of the present invention provides a unique dummy load which dampens the standing wave patterns generated by the closed cavity design of microwave ovens and, at the same time, provides a large sample processing area or surface. The apparatus minimizes the effects of standing wave patterns over the processing surface. The processing surface displays substantially uniform properties with respect to microwave sample heating when measured by thermographic paint, liquid crystal sheets, neon bulb arrays and experimental evaluation. As a result, the apparatus ensures that currently existing microwave ovens are now suitable for biomedical applications and research endeavors. The apparatus also ensures that microwave-assisted processing is now on a par with mechanical and bench methods on the basis of run-to-run reproducibility that is now, but was not previously, possible with currently existing microwave ovens.

Accordingly, the present invention is directed to an apparatus for dampening standing wave pattern generation in a closed cavity of a microwave oven. The apparatus includes a fluid table having an enclosure made of a microwave energy transparent material and means, such a generally flat top platform made of glass and held in place by the enclosure, for defining a processing surface for placement thereupon of samples to be processed. The apparatus also includes a quantity of dielectric fluid, such as water or fluid having dielectric properties similar to water, contained by the enclosure so as to provide a large flat surface of the dielectric fluid underneath the flat platform and thus below the processing surface. The apparatus further includes means for recirculating the dielectric fluid to and from the enclosure of the fluid table and for cooling the dielectric fluid to maintain the dielectric fluid within a given range of temperatures. The processing surface on the flat platform is used for placement of tissue samples, in containers, on slides or in a vacuum. The processing surface, the underlying dielectric fluid, and the control of the temperature of the dielectric fluid combine to provide uniform sample temperature control by mitigating energy density differences from standing wave patterns generated in the closed cavity of the microwave oven. The enclosure and dielectric fluid contained therein serve as a microwave energy sink that is maintained under relatively constant conditions and is of such a depth as to preclude the formation of standing wave patterns on the processing surface of the flat platform of the apparatus.

The apparatus of the present invention thus provides a processing surface available for use during microwave-assisted processing of samples for various biomedical, pharmaceutical, biological, industrial, agricultural or veterinary biomedical applications. More specifically, representative applications are processing of tissue specimens into paraffin or resins, special stain applications, epitope (antigen) retrieval, immunocytochemistry and decalcification.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a schematic diagram of an apparatus of the present invention for dampening standing wave pattern generation in a closed cavity of a microwave oven.

FIG. 2 is a perspective view of an exemplary embodiment of a fluid table of the apparatus.

DETAILED DESCRIPTION OF THE INVENTION

Figure 3:
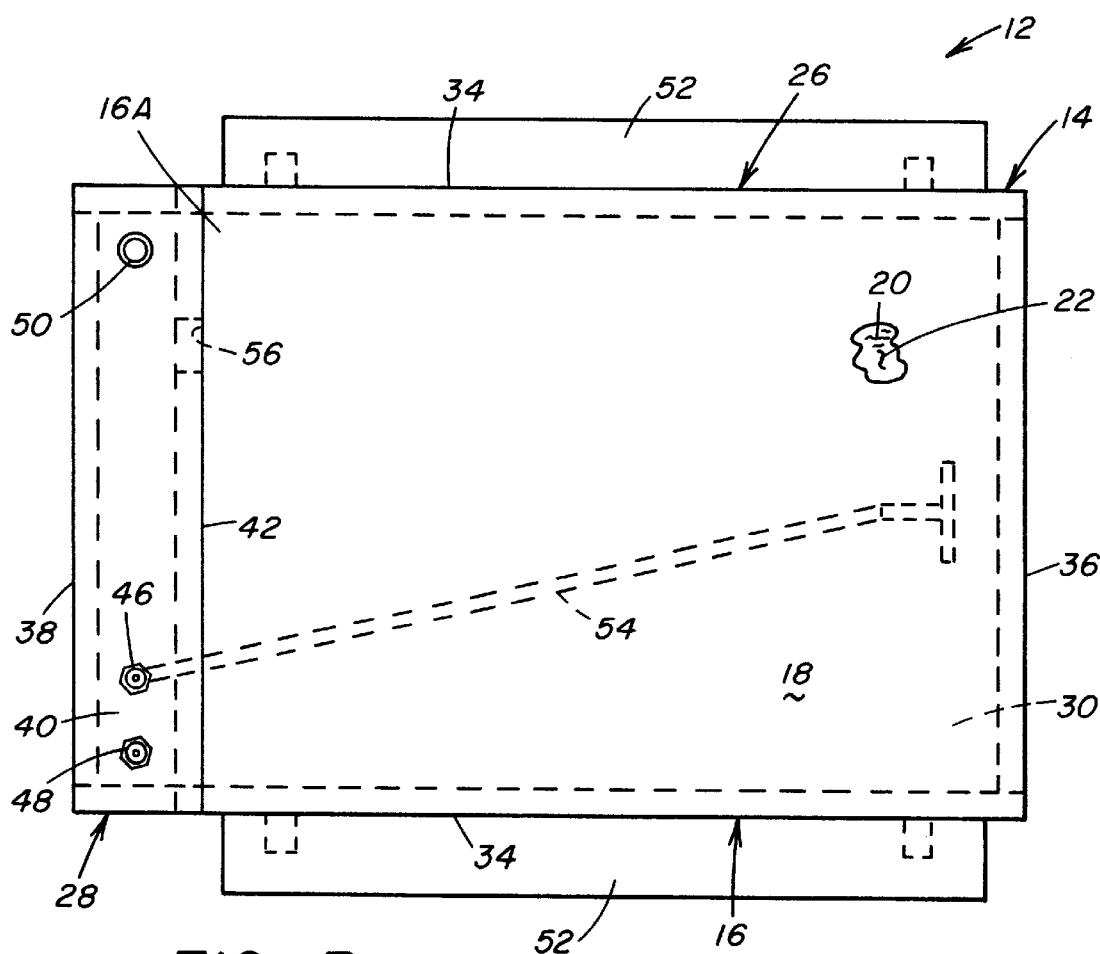
FIG. 3 is a top plan view of the fluid table of the apparatus.

Referring to the drawings and particularly to FIG. 1, there is illustrated a schematic diagram of an apparatus of the present invention, generally designated 10, for dampening standing wave pattern generation in a closed cavity of a microwave oven (not shown). The apparatus 10 includes a fluid table 12 having an enclosure 14 made of a suitable microwave energy transparent material, such as plastic, and means, such a generally flat top platform 16 made of a suitable material, such as glass, and held in place by the enclosure 14, for defining a processing surface 18 for placement thereupon of samples (not shown) to be processed. The apparatus 10 also includes a quantity of dielectric fluid 20, such as water or fluid having dielectric properties similar to water, contained by the enclosure 14 so as to provide a large flat surface 22 of the dielectric fluid 20 underneath the top flat platform 16 and thus below the processing surface 18. The apparatus 10 further includes means 24 for recirculating the dielectric fluid 20 to and from the enclosure 14 of the fluid table 12 and for cooling the dielectric fluid 20 to maintain the recirculated dielectric fluid 20 within a given range of temperatures, such as from 25 to 45 degrees C. The processing surface 18 on the flat platform 16 is used for placement of tissue samples (not shown), in containers, on slides or in a vacuum. The processing surface 18, the underlying dielectric fluid 20, and the control of the temperature of the dielectric fluid 20 combine to provide uniform sample temperature control by mitigating energy density differences from standing wave patterns that are generated in the closed cavity microwave oven. The enclosure 14 and the dielectric fluid 20 contained therein serve as a microwave energy sink that is maintained under relatively constant conditions and is of such a depth as to preclude the formation of standing wave patterns on the processing surface 18 of the flat platform 16 of the apparatus 10.

Figure 4:
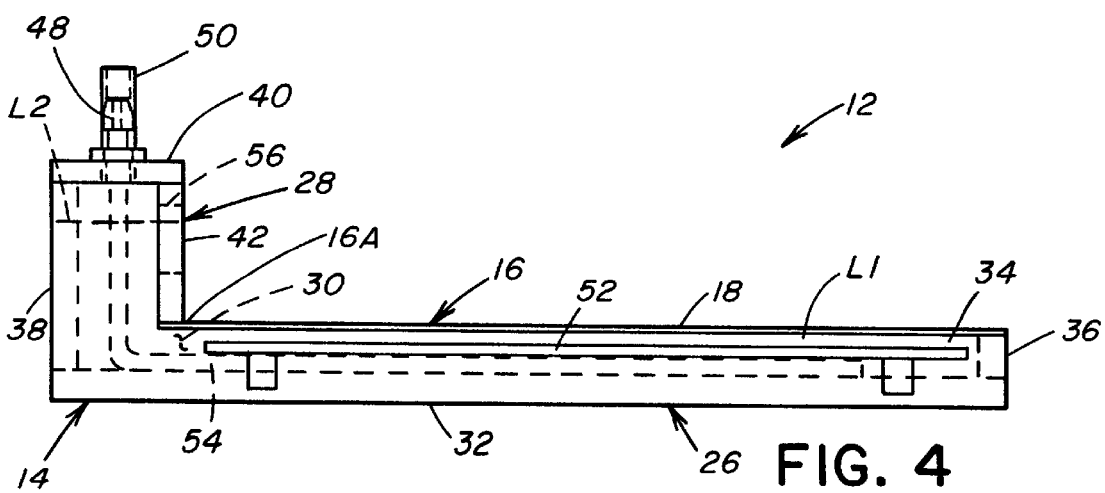
FIG. 4 is a side elevational view of the fluid table of the apparatus.

Referring now to FIGS. 2 to 4, there is illustrated an exemplary embodiment of the fluid table 12 of the apparatus 10. The fluid table 12 is adapted to be placed in a microwave irradiation cavity of a microwave oven (not shown). The enclosure 14 of the fluid table 12 is in the form of a dual level water trough having a horizontally-extending main portion 26 and a vertically-extending end portion 28 attached at one end of the main portion 26 so as to provide the enclosure 14 with an overall L-shaped configuration and define a water-tight interior reservoir 30 having the same configuration. The tabletop-like flat platform 16 is mounted on the main portion 26 of the enclosure 14 so as to define the sample-receiving processing surface 18 with the interior reservoir 30 of the enclosure 14 mainly formed under and coextensive with the platform 16 but also rising above the platform 16 at one end 16A thereof such that the quantity of dielectric fluid 20 contained in the interior reservoir 30 provides dual (lower and upper) surface levels L1, L2 respectively below and above the platform 16. The vertical end portion 28 of the enclosure 14 provides a means to eliminate air bubbles formed in the interior reservoir 30 of the horizontal main portion 26 of the enclosure 14.

The enclosure 14 of the fluid table 12 is formed by a bottom panel 32, a pair of opposite side panels 34, a front panel 36, a rear back end panel 38, a rear top panel 40 and a rear front end panel 42. The panels 32–42 are fixedly interconnected together at their respective peripheral edges so as to defined the horizontal main portion 26 and the vertical end portion 28 and the interior reservoir 30 having the overall L-shaped configurations. The panels 32, 42 also define an upper opening 44 of the enclosure 14 which is covered by the tabletop-like flat platform 16. The flat platform 16 of the fluid table 12 is a plate preferably made of a glass material, while the remaining panels 32–42 are made of a plastic material invisible to microwaves. Construction parts should be consistent with minimized or zero microwave energy absorption. While an enclosure 14 constructed of separate parts is illustrated, it is readily understood that many of the parts of the enclosure 14 can be molded as onepiece units so as to reduce the number of separate parts that have to be assembled or attached together to construct the enclosure 14.

The fluid table 12 further includes an inlet fixture 46, an outlet fixture 48, a port 50 on the enclosure 14 for venting air bubbles from the vertical end portion 28 of the enclosure 14 and for mounting measuring and/or control devices, such as temperature measurement of the dielectric fluid 20, in the interior reservoir 30, and one or more specimen stabilizers in the form of shelves 52 supported on and extending outwardly in opposite directions relative to one another from opposite side panels 34 of the enclosure 14. The inlet and outlet fixtures 46, 48 are spigots provided for the dielectric fluid 20 to enter and exit the interior reservoir 30. The outlet fixture 48 also can have a length of tubing 54 which reaches into the interior reservoir 30 to a location adjacent to the front panel 36 of the enclosure 14 so that the dielectric fluid 20 is drawn from the interior reservoir 30 only after it has flowed throughout the interior reservoir 30 from the inlet fixture 46, permitting efficient recirculation of the dielectric fluid 20. Other entry ports can be provided for certain other measurements. Also, a water level window 56 can be provided in the rear front end panel 42 through which to observe the upper level L2 of the dielectric fluid 20 in the vertical end portion 28 of the enclosure 14.

The flow of dielectric fluid 20 is controlled by the recirculating and cooling means 24 which can take the form of a conventional fluid flow pump (not shown) and conventional heat exchanger (not shown) located outside of the microwave cavity and interconnected to the fluid table 12 by suitable means such as lengths of silicone rubber tubing (not shown) extending between an outlet and an inlet of the pump and the inlet and outlet fixtures 46, 48 of the fluid table 12. Special stainless steel tubings (not shown) are installed in a cavity wall of the microwave oven to connect the two lengths of silicone rubber tubing between the pump and the fluid table 12.

The specimen stabilizer shelves 52 placed on either side of the fluid table 12 hold or support the items for sample processing. Under these conditions, scientists, histologists, pathologists, botanists, engineers and other disciplines may place samples or objects upon the flat platform 16 in the microwave oven cavity. Flow of the dielectric fluid 20 is then initiated between the recirculating and cooling means 24 outside the microwave oven cavity and the fluid table 12 inside. The fluid temperature is controlled by suitable means in which the warm fluid leaving the fluid table 12 runs through the recirculating and cooling means 24 and means for temperature measurement and control (not shown) and then flows back to the fluid table 12.

The temperature maintenance of the recirculated dielectric fluid 20 creates a relatively uniform temperature condition, within a narrow temperature range of 5 degrees C. across the processing surface 18 of the platform 16 of the fluid table 12. Uniformity of temperature on the platform 16 allows samples to be processed under identical conditions with great speed and quality, which can be important for many types of tissue and cell staining and other sample type processing using microwave energy. Prior art hot spot detection methods, such as liquid crystal sheets and neon bulb arrays, were employed to visually demonstrate and confirm that no hot spots were present over the entire sample supporting surface 18 of the platform 16 of the fluid table 12. The fluid table 12 of the apparatus 10 thus provides a sample processing area having dimensions which exceed those which can be created by beaker water loads and provides a smoothing of the standing wave patterns in a microwave cavity in which the fluid table 12 is utilized so that hot spots are diminished to the degree that they do not interfere with sample processing protocols.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

We claim:

1. An apparatus for dampening standing wave pattern generation in a closed cavity of a microwave oven on an exterior sample processing surface provided by said apparatus, said apparatus comprising:

(a) a fluid table having an enclosure made of a microwave energy transparent material and defining an interior reservoir, and a platform held in place by said enclosure defining a sample processing surface exteriorly on said platform and overlying said interior reservoir for placement of samples to be processed upon said exterior sample processing surface of said platform;

(b) a quantity of dielectric fluid contained by said interior reservoir of said enclosure of said fluid table so as to provide a large flat surface of said dielectric fluid underneath said exterior sample processing surface, said enclosure and dielectric fluid contained in said interior reservoir thereof serving as a microwave energy sink underlying said platform being maintainable under such conditions and having such depth as to minimize formation of standing wave patterns on said exterior sample processing surface of said platform; and (c) means attached to said enclosure for allowing said dielectric fluid to enter and exit said interior reservoir of said enclosure.

2. The apparatus of claim 1 wherein said enclosure is made of plastic.

3. The apparatus of claim 1 wherein said platform defining said exterior sample processing surface is generally flat.

4. The apparatus of claim 3 wherein said enclosure has at least one shelf thereon extending outwardly from a side of said flat platform.

5. The apparatus of claim 3 wherein said flat platform is made of glass.

6. An apparatus for dampening standing wave pattern generation in a closed cavity of a microwave oven on an exterior sample processing surface provided by said apparatus, said apparatus comprising:

(a) a fluid table having an enclosure made of a microwave energy transparent material and a platform held in place by said enclosure defining a sample processing surface exteriorly on said platform for placement thereupon of samples to be processed; and (b) a quantity of dielectric fluid contained by said enclosure of said fluid table so as to provide a large flat surface of said dielectric fluid underneath said exterior sample processing surface, said enclosure and dielectric fluid contained therein serving as a microwave energy sink being maintainable under such conditions and having such depth as to minimize formation of standing wave patterns on said exterior sample processing surface of said platform;

(c) said enclosure including a horizontal main portion and a vertical end portion attached at one end of said horizontal main portion so as to provide said enclosure with an overall L-shaped configuration and define a water-tight interior reservoir having the same configuration as said enclosure and extending between and within said horizontal main portion and vertical end portion of said enclosure so that dual water surface levels are provided respectively in said horizontal main portion and said vertical end portion of said enclosure by said quantity of dielectric fluid in said interior reservoir thereof, said platform being seated on said horizontal main portion, said interior reservoir being mainly located in said horizontal main portion of said enclosure under and coextensive with said platform but also rising in said vertical end portion of said enclosure above said platform at one end thereof such that said dual water surface levels comprise a lower surface level provided in said horizontal main portion below said platform and an upper surface level provided in said vertical end portion above the level of said platform.

7. The apparatus of claim 6 wherein said vertical end portion has space therein above said upper surface level providing a region for accumulation of air bubbles from said interior reservoir in said horizontal portion of said enclosure.

8. The apparatus of claim 7 wherein said enclosure has a port on said vertical end portion thereof being operable to allow venting of the air bubbles therefrom.

9. The apparatus of claim 6 wherein said enclosure has a pair of inlet and outlet fixtures on said vertical end portion thereof to allow dielectric fluid to enter and exit said interior reservoir of said enclosure.

10. An apparatus for dampening standing wave pattern generation in a closed cavity of a microwave oven on an exterior sample processing surface provided by said apparatus, said apparatus comprising:
    (a) a fluid table adapted to fit within a cavity of a microwave oven and having an enclosure made of a microwave energy transparent material and defining an interior reservoir, and a platform held in place by said enclosure defining a sample processing surface exteriorly on said platform and overlying said interior reservoir for placement of samples to be processed upon said exterior sample processing surface of said platform;
    (b) a quantity of dielectric fluid contained by said interior reservoir of said enclosure of said fluid table so as to provide a large flat surface of said dielectric fluid underneath said exterior sample processing surface, said enclosure and dielectric fluid contained in said interior reservoir thereof serving as a microwave energy sink underlying said platform and being maintainable under such conditions and having such depth as to minimize formation of standing wave patterns on said exterior sample processing surface of said platform; and
    (c) means for recirculating said dielectric fluid to and from said interior reservoir of said enclosure of said fluid table and for cooling said dielectric fluid to maintain the temperature of said dielectric fluid within a given range, said processing surface, underlying dielectric fluid and control of said temperature of said dielectric fluid coacting to provide substantially uniform sample temperature control by mitigating energy density differences from standing wave patterns generated in a closed cavity of a microwave oven.

11. The apparatus of claim 10 wherein said enclosure is made of plastic.

12. The apparatus of claim 10 wherein said platform defining said exterior sample processing surface is generally flat.

13. The apparatus of claim 12 wherein said enclosure has at least one shelf thereon extending outwardly from a side of said flat platform.

14. The apparatus of claim 12 wherein said flat platform is made of glass.

15. An apparatus for dampening standing wave pattern generation in a closed cavity of a microwave oven on an exterior sample processing surface provided by said apparatus, said apparatus comprising:
    (a) a fluid table having an enclosure made of a microwave energy transparent material and a platform held in place by said enclosure defining a sample processing surface exteriorly on said platform for placement thereupon of samples to be processed;
    (b) a quantity of dielectric fluid contained by said enclosure of said fluid table so as to provide a large flat surface of said dielectric fluid underneath said exterior sample processing surface, said enclosure and dielectric fluid contained therein serving as a microwave energy sink being maintainable under such conditions and having such depth as to minimize formation of standing wave patterns on said exterior sample processing surface of said platform, said enclosure including a horizontal main portion and a vertical end portion attached at one end of said horizontal main portion so as to provide said enclosure with an overall L-shaped configuration and define a water-tight interior reservoir having the same configuration as said enclosure and extending between and within said horizontal main portion and vertical end portion of said enclosure so that dual water surface levels are provided respectively in said horizontal main portion and said vertical end portion of said enclosure by said quantity of dielectric fluid in said interior reservoir thereof, said platform being seated on said horizontal main portion, said interior reservoir being mainly located in said horizontal main portion of said enclosure under and coextensive with said platform but also rising in said vertical end portion of said enclosure above said platform at one end thereof such that said dual water surface levels comprise a lower surface level provided in said horizontal main portion below said platform and an upper surface level provided in said vertical end portion above the level of said platform; and
    (c) means for recirculating said dielectric fluid to and from said interior reservoir of said enclosure at said vertical end portion thereof and for cooling said dielectric fluid to maintain the temperature of said dielectric fluid within a given range, said processing surface, underlying dielectric fluid and control of said temperature of said dielectric fluid coacting to provide substantially uniform sample temperature control by mitigating energy density differences from standing wave patterns generated in a closed cavity of a microwave oven.

16. The apparatus of claim 15 wherein said vertical end portion has space therein above said upper surface level providing a region for accumulation of air bubbles from said interior reservoir in said horizontal portion of said enclosure and a port on said vertical end portion being operable to allow venting of the air bubbles therefrom.

17. The apparatus of claim 15 wherein said enclosure has a pair of inlet and outlet fixtures on said vertical end portion thereof to allow dielectric fluid to enter and exit said interior reservoir of said enclosure from and to said recirculating and cooling means.

* * * * *